United States Patent [19]
Paul et al.

[11] Patent Number: 5,320,139
[45] Date of Patent: Jun. 14, 1994

[54] FLUID DELIVERY SYSTEM

[75] Inventors: Carlton H. Paul, Groton; Russell L. Keene, Jr., Sudbury, both of Mass.

[73] Assignee: Millipore Corporation, Bedford, Mass.

[21] Appl. No.: 40,320

[22] Filed: Mar. 30, 1993

[51] Int. Cl.⁵ .............................................. F16K 11/20
[52] U.S. Cl. .................................... 137/567; 137/597; 137/606
[58] Field of Search ............... 137/565, 606, 884, 567, 137/597; 251/367

[56] References Cited

U.S. PATENT DOCUMENTS

| | | | |
|---|---|---|---|
| 3,884,255 | 5/1975 | Merkle | 137/565 X |
| 4,168,724 | 9/1979 | Graffunder et al. | 137/606 |
| 4,254,797 | 3/1981 | Mayeau | 137/565 |
| 4,304,257 | 12/1981 | Webster | 137/597 X |
| 4,597,412 | 7/1986 | Stark | 137/606 |
| 4,773,446 | 8/1988 | Farnsworth et al. | 137/606 |
| 5,095,938 | 3/1992 | Garrison | 137/597 X |

*Primary Examiner*—Stephen M. Hepperle
*Attorney, Agent, or Firm*—Andrew T. Karnakis; Paul J. Cook

[57] ABSTRACT

A fluid delivery system is provided to deliver precise volumes of a plurality of fluid in sequence to one or more treatment reservoirs. Fluid channels are formed in a plate structure to provide a means for delivering fluids from a plurality of fluid reservoirs to one or a plurality of treatment reservoirs. Each fluid is delivered by a system comprising a pneumatically or electrically activated inlet valve in fluid communication with a fluid reservoir, a positive displacement pump in fluid communication with the inlet valve and a pneumatically or electrically activated outlet valve in fluid communication with the positive displacement pump.

8 Claims, 11 Drawing Sheets

FLUID DELIVERY SYSTEM

BACKGROUND OF THE INVENTION

This invention relates to a fluid delivery system for delivering a plurality of fluids, in sequence to one or more treatment reservoirs.

Prior to the present invention, fluid delivery systems have been available which minimize intermixing of fluids while delivering a precise amount of a fluid for chemical reaction. These systems are generally utilized for chemical processes involving a large number of sequentially effected chemical reactions such as in protein synthesis, DNA synthesis or when sequencing proteins.

U.S. Pat. No. 4,008,736 discloses a valve block containing a capillary formed of capillary segments bored at about 30° from a contact surface of the block. The junctions of the capillary segments are effected at the contact surface and within the block. The junctions at the contact surfaces form valving sites to which are engaged apertured sliding blocks which effect fluid communication with the capillary. While the sliding blocks are effective in providing the desired fluid flow, they wear too rapidly thereby causing undesirable leaks.

U.S. Pat. No. 4,168,724 discloses a similar device but replaces the slider valves with diaphragm valves. The fluid is delivered through the valves from a pressurized fluid storage source. This system requires a vacuum assist to open the valves. This system is undesirable because the type of diaphragm valve used is undesirably susceptible to particulate contamination. In addition, the pressure drop through the valves is difficult to control which causes less accurate reagent delivery.

U.S. Pat. No. 4,558,845 discloses a fluid delivery system utilizing a valve block assembly comprising a separate block for each valve site. The common conduit to the reaction site is alternately a channel in a block and tubing connecting two adjacent blocks. This arrangement requires a plurality of fittings which are subject to leaking.

U.S. Pat. No. 4,773,446 discloses a valve block assembly which utilizes diaphragm valves. The valves serve to control fluid flow from a plurality of pressurized fluid reservoirs, in sequence to a common outlet reservoir. This system requires the use of conduits from the fluid reservoirs and fittings to valve blocks for each conduit.

The fluid delivery system of the prior art depend upon the use of positive pressure to deliver the fluid and upon the control of back pressure to the fluid reservoir in order to precisely control the amount of fluid delivered to a treatment reservoir. These systems require the frequent adjustment of the fluid delivery means as a function of back pressure. All of the systems set forth above depend upon the precise control of reservoir pressure and restriction through the tubing, channels, and valves to control reagent delivery volume. They are very sensitive to variations of the removable reaction columns as regards the delivery volume and flow rate. Also, these systems deliver fluids against backpressures only up to about 10 psig.

U.S. Pat. No. 5,123,443 discloses a system for delivering a plurality of fluids in sequence to a treatment reservoir, comprising a plurality of pumps in fluid communication with other via passages in a solid plate. Each pump is comprised of a diaphragm member that effects transport by forcing fluid out of a plenum cavity; an injector (check valve) that opens in response to a threshold pressure to allow escape of fluid into a common passage; and an inlet check valve that closes in response to rising pressure but otherwise allows the plenum cavity of the diaphragm member to refill. The performance of these passive check valves in pumps of very small volume is marginal because even very small leaks greatly dampen the pressure transients to which these check valves respond. The worst case situation is the attempt to pump a low viscosity, compressible fluid (i.e., gas), wherein the pumps may display difficulty in priming due to microscopic leaks.

Copending U.S. patent application Ser. No. 07/655,012, filed Feb. 14, 1991, and entitled "Conduit Plate for Fluid Delivery System" discloses a conduit plate for a fluid delivery system comprising four or five layers laminated together, including a plurality of notched openings for attaching external fluid processing components in fluid communication with the plate; and a single fluid conduit layer for effecting passage of fluids between different points on the solid plate. The plate, preferentially is formed of a ceramic material. A plurality of fluids are delivered in sequence to a desired point by means of a plurality of pumps, each comprising a diaphragm member, an injector (a passive outlet check valve), and an inlet check valve. The notched openings in the plate address a problem inherent in the manufacture of the solid plate wherein the dimensional tolerances of the solid plate are comparable or larger than the dimensions of the passages within the plate so that mating parts can be aligned accurately only insofar as the plate itself serves to key the positions of external components mating to said plate. However, direct attachment of components to the solid plate places the solid plate under tensional forces that may cause breakage. The presence of a single conduit layer in the solid plate results in unique layout of fluid passages in the plate because passages cannot cross each other, and revisions in the fluid path are correspondingly made more difficult. Apparatus which utilize these plates are disclosed in U.S. Pat. Nos. 5,095,932; 5,095,938; 5,111,845 and 5,123,443.

It would be desirable to provide a system which eliminates the need of adjustment of the fluid delivery means. It would also be desirable to utilize a means to deliver accurate fluid volumes which is insensitive to back pressure. Such a system would result in improved system performance and reduced reagent consumption. It would also be desirable to provide a fluid delivery system which minimizes the use of tubes and tube fittings while minimizing the volume of the system as compared to presently available systems. In addition, it would be desirable to provide a fluid delivery system which can be easily primed so that even gases can be pumped easily.

SUMMARY OF THE INVENTION

The present invention provides a system for delivering a plurality of fluids in sequence to a treatment reservoir wherein a chemical reaction or a physical treatment step occurs. The different fluids are delivered to a given location such as a treatment reservoir by means of a plurality of positive displacement pumps, each allocated to a different reagent and in fluid communication with each other via passages in a solid plate.

Each pump is comprised of a diaphragm member and two pneumatically or electrically controlled gates in communication via passages in a solid plate. The diaphragm member comprises a flexible diaphragm that moves within a plenum (cavity), serving thereby to eject a fixed volume of fluid from the pump. The volume of the plenum generally can be as small as two microliters and as large as two milliliters. The controlled gates allow the diaphragm member to refill from one direction and eject its contents under pressure in the same or in a second direction. The controlled gates improve on the performance of presently available check valves by greatly reducing the pressure drop through open valves, thereby rendering priming of the pumps highly reliable and allowing a wide range of practical volumes for the plenum cavity. The actuation of the controlled gates can be synchronized such that the pump will operate in either of two directions, or allow free flow of fluid through the pump.

All components of the fluid delivery system that mate with the solid plate member (diaphragm members, controlled gates, port connectors) are positioned and secured by external metal plates. The metal plates are secured to each other by fasteners passing through the solid plate member. All the mating components are pressed firmly against respective surfaces of the solid plate member by spring means, all the mating components are designed to allow acceptable dimensional errors in their alignment with the solid plate member.

The controlled gates, diaphragm members and port connectors can be connected to both faces of the plate structure, thereby increasing the component density (and halving the size of the solid plate) and decreasing the length of innerconnecting passages within the solid plate as compared to a plate structure wherein the external components are on only one surface. The external components preferentially are arranged on a regular grid to simplify the layout and alignment of parts in the final assembly. In another embodiment, all components can be connected to a single face of the ceramic plate. In this embodiment multiple ceramic plates can be interconnected as modules.

DESCRIPTION OF SPECIFIC EMBODIMENTS

In accordance with this invention, a fluid delivery system is provided which comprises a solid plate containing conduits and a plurality of fluid transport means for effecting fluid passage through the conduits. The system is constructed to effect transport of a plurality of fluids sequentially from a plurality of fluid reservoirs to at least one treatment reservoir. Means are provided for maintaining an elevated pressure in the fluid reservoirs. The means for transporting each fluid comprises a positive displacement diaphragm member and two solenoid or pneumatic controlled gates. One gate is connected to a source of fluid and is in fluid communication with the diaphragm pump and the second gate which, in turn is in fluid communication with a reaction column. The system of this invention is particularly suitable for use in processes under carefully controlled conditions. Examples of such processes include synthesis of biopolymers such as nucleic acid, peptides or carbohydrates. These processes require sequential chemical reactions which are alternated with washing steps to remove excess unreacted reagent. In some instances, the reagents require a particular atmospheric environment such as an inert environment or an oxidizing environment. In these instances, gases are provided to the fluid reservoir. Therefore, these processes require fluid delivery systems wherein reagent, processing chemicals and gases are processed in a precise manner so that precise volumes of fluid are delivered to the appropriate destination within the system at the proper time and within the proper sequence. When a plurality of treatment reservoirs are utilized, switching means are provided to direct the appropriate reagent, process chemical or gas to the appropriate treatment reservoir.

The plate utilized in the system of this invention contains the conduits for fluid transport formed from a plurality of thinner ceramic plates laminated together by application of very high temperatures. Each of the thinner component plates can be fabricated by a photolithographic process wherein a specified pattern is imprinted with ultraviolet light in the component layer by means of a mask, followed by selective etching of the exposed ceramic surfaces to create the specified pattern in the component plate.

Figure 1:
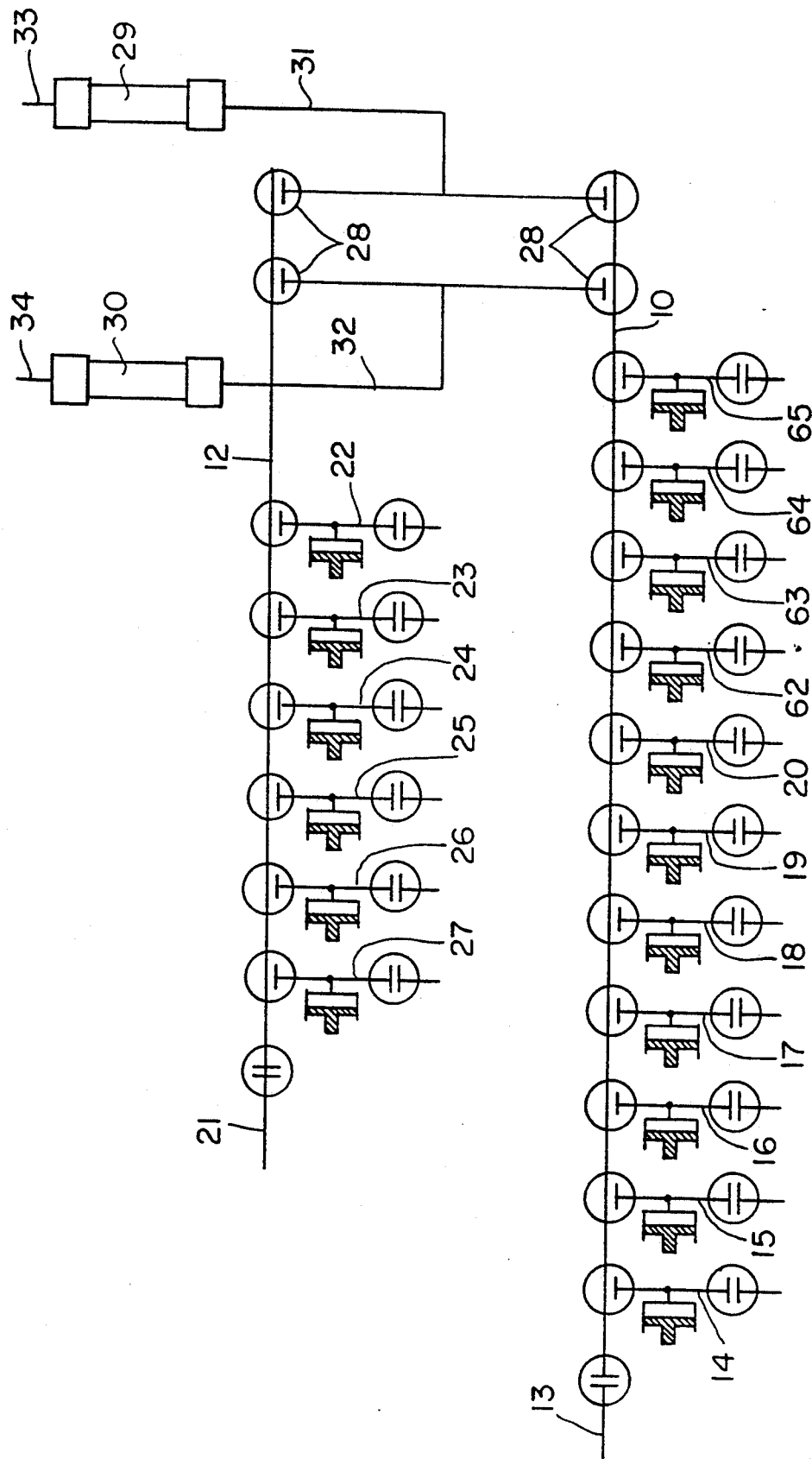
FIG. 1 is a schematic view of a system useful for producing DNA and utilizing a plate structure of this invention.

The system of the invention will be described specifically, for convenience with reference to a process for producing polymeric nucleic acids (NA). Referring to FIG. 1 a process for making NA is shown schematically. The process shown utilizes two sets of fluid reagents with one set in fluid communication with common channel 10 and a second set in fluid communication with common channel 12. The first set includes a gas flow-through means for purging the system, (Gas B) connected to channel 13, acetonitrile (ACN-B) connected to channel 14, tetrazole (TET) connected to channel 15, an auxiliary reservoir connected to channel 16, an auxiliary reservoir connected to channel auxiliary amdt 7 connected to channel, an auxiliary reservoir connected to channel 18, an auxiliary reservoir connected to channel 19, an auxiliary reservoir connected to channel 20, thymidine (T) connected to channel 64 and adenosine (A) connected to channel 65. The second set of fluids includes a gas flow-through means for purging the system (GAS-A) connected to channel 21, acetonitrile (ACN-A) connected to channel 27, capping solution A (CAP-A) connected to channel 26, capping solution B (CAP-B) connected to channel 25, oxidizer (OXI) connected to channel 23, dichloroacetic acid (DCA) connected to channel 22 and auxiliary oxidation reagent reservoir (OX 2) connected to channel 24. The reagents, adenosine, cytidine, guanosine and thymidine are reagents used to form the DNA as is well known in the art. GAS-A provides the function of purging the system and transporting small volumes of liquid out of the system to a detector. GAS-B provides the same function as GAS-A. Acetonitrile provides the function of rinsing the system. Acetic anhydride (CAP-A) and N-methylimidazole (CAP-B) provides the function of terminating unreacted sites to prevent further elongation of the failed sequence. OXI or OX 2 such as iodine in water and pyridine provides the function of oxidizing the elongated polymeric chain to stabilize the internucleotide phosphate linkages. DCA provides the function of deprotecting the bound residue to permit further condensation reaction. TET provides the function of activating the reactive monomer for the next coupling reaction. Partition valve 28 serves as a switch to direct fluid from either channel 10 or channel 12 to either treatment reservoir 29 comprising a reaction column containing a solid support such as controlled pore glass (CPG) or a membrane through channel 31 or treatment column 30 which is a duplicate of column 29 through channel 32. Channels 33 and 34 direct processed fluid to waste or a detector.

Figure 2:
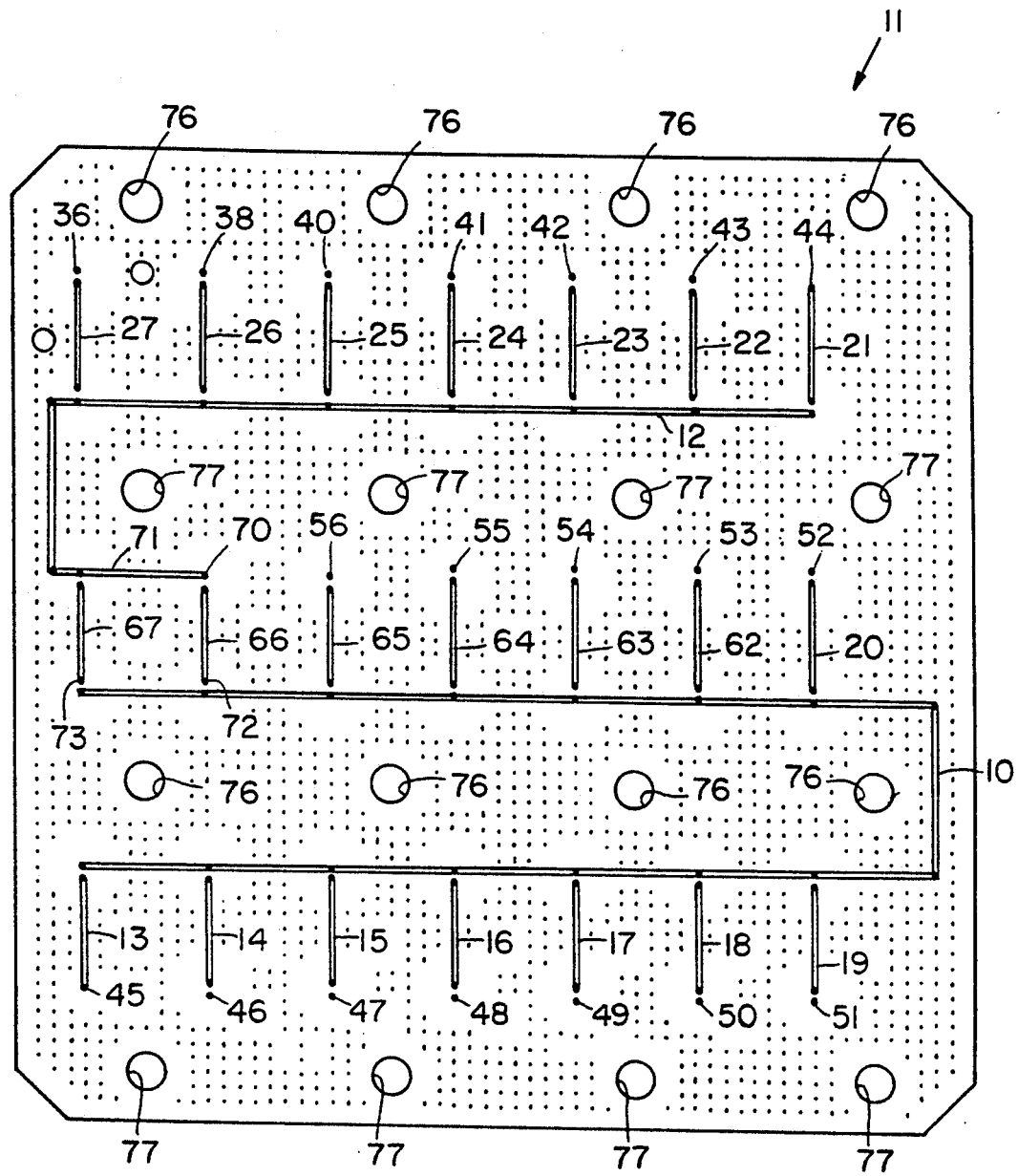
FIG. 2 is a top view of all five layers of FIGS. 1a, 1b, 1c, 1d and 1e aligned in the configuration of the final solid plate structure of this invention.

FIG. 2 shows the plate holes and arrangement of conduits for processing fluids through the plate structure 11. The conduits include the A train 12 and the B train 10. Conduit 27 is a conduit connected to an auxiliary reservoir through tubing (not shown) and hole 36 (FIG. 2). Conduit 26 is a conduit connected to a container for dichloroacetic acid through tubing (not shown) and hole 38. Conduit 25 is a conduit for an oxidizer from a container through tubing (not shown) and hole 40. Conduit 24 is a conduit for N-methylimidazole from a container through tubing (not shown) and hole 41. Conduit 23 is a conduit for acetic anhydride from a container through tubing (not shown) and hole 42. Conduit 22 is a conduit for acetonitrile from a container through tubing (not shown) and hole 43. Conduit 21 is a conduit for purging gas from a container through tubing (not shown) and hole 44. Conduit 13 is a conduit for a purging gas to be introduced through hole 45. Conduit 14 is a conduit for acetonitrile from a container through tubing (not shown) and hole 46. Conduit 15 is a conduit for tetrazole from a container through tubing (not shown) and hole 47. Conduit 16 is a conduit for a reagent from an auxiliary reservoir from a container through tubing (not shown) and the hole 48. Conduit 17 is a conduit for adenosine from a container through tubing (not shown) and the hole 49. Conduit 18 is a conduit for cystidine from a container through tubing (not shown) and the hole 50. Conduit 19 is a conduit for guanosine from a container positioned over the hole 51. Conduit 20 is a conduit for thymidine from a container through tubing (not shown) and the hole 52. Conduit 62 is a conduit for thymidine from a container through tubing (not shown) and the hole 53. Conduit 63 is a conduit for cytidine from a container through tubing (not shown) and the hole 54. Conduit 64 is a conduit for guanosine from a container through tubing (not shown) and the hole 55. Conduit 65 is a adenosine from a container through tubing (not shown) and the hole 56.

Figure 1A:
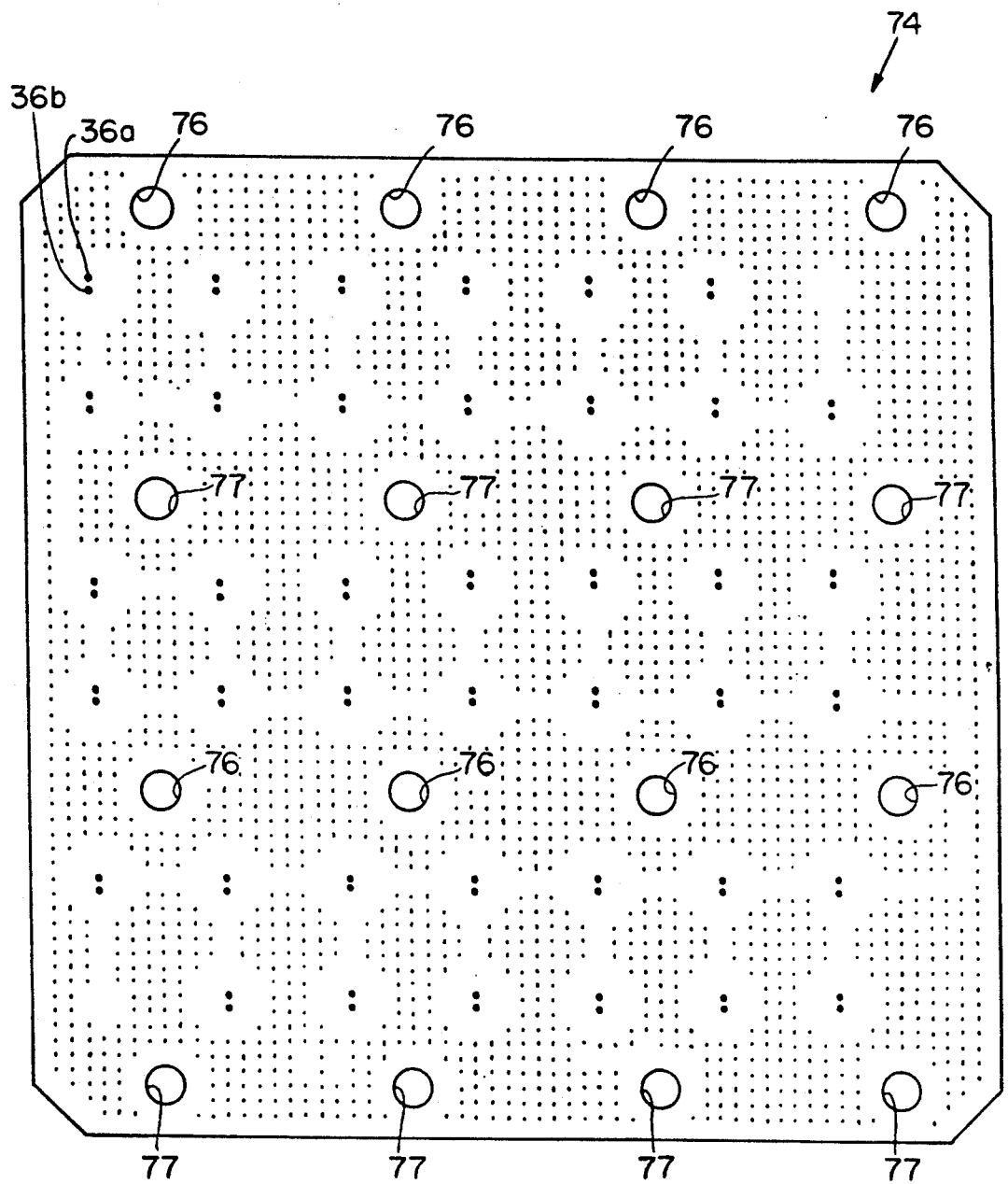
FIG. 1a is a view of the top layer of the plate structure of this invention.
Figure 3:
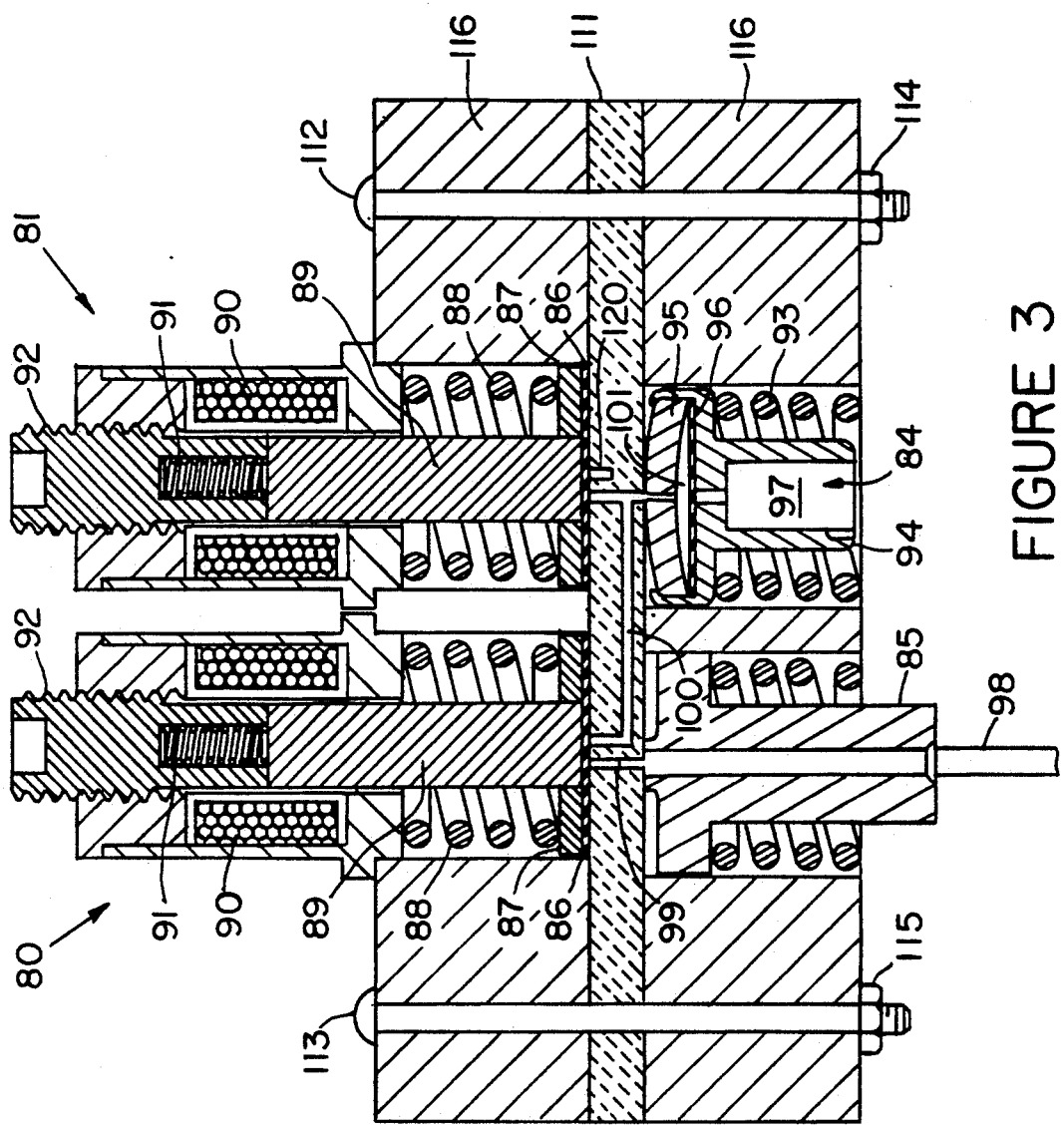
FIG. 3 is a section view of the fluid pumping means of this invention which is used with or positioned on opposing surface of the plate structure of FIGS. 1a–1e to form the system of this invention.

The partition valve 28 serves to direct reagent from either the A-Train 12 or the B-Train 10 to reaction column positioned over holes 70, 71, 72, or 73. The partition valve 28 is formed of a multiplicity of gates described specifically with reference to FIG. 3. The fluid delivery system is best described with reference to FIG. 3. The plate 74 shown in FIG. 1a has a plurality of adjacent holes, exemplified by holes 36a and 36b, each set being used in conjunction with a solenoid or pneumatic valve 80 or 81 shown in FIG. 3. In addition, the fluid delivery system of this invention will be described specifically with reference to the use of solenoid valves. The remainder of the sets of adjacent holes are not labeled for convenience. The plate 75 having single spaced apart holes shown in FIG. 1e is used in conjunction with a diaphragm pump 84 and a source of fluid to be transported 85. The solenoid valve 81 comprises an outlet valve while the solenoid valve 80 comprises an inlet valve. The solenoid valves 80 and 81 each include a diaphragm 86, a thrust washer 82, a spring 88 and an armature 89. The upper portions of the solenoid valves 80 and 81, include a coil 90, a spring 91 and an adjustable stop 92. The diaphragm pump 84 is a positive displacement pump and comprises a spring 93, a top insert member 94, a bottom insert member 95, and a diaphragm 96. The insert members 94 and 95 are crimped together to secure the diaphragm 96. Insert 94 contains a cavity 97 to connect to a fluid source which can be opened or closed to alternately apply or remove a pressure on the top surface of diaphragm 96. Fluid to be transported enters port 98 and channel 99 when diaphragm 86 of solenoid valve 80 is opened. When diaphragm 96 of pump 84 is vented to atmosphere and diaphragm 86 of valve 80 is opened, fluid passes through channel 100 into plenum 101 of pump 84. When diaphragm 86 of valve 80 is closed and pneumatic pressure is applied to the diaphragm 96 of pump 84, and diaphragm 86 of valve 81 is open, fluid passes into channel 120 which is the same as channel 12 in the case of the A Train or channel 10 in the case of the B Train (See FIG. 1). The positioning of the diaphragm 86 of solenoid valves 80 and 81 and of the diaphragm 96 of pump 84 are controlled to prevent flow of fluid from the outlet solenoid valve 81 toward the diaphragm pump 84. The diaphragm positioning is controlled by means of the solenoids 92 and fluid pressure in cavity 97 which are, in turn controlled by conventional control means such as a microprocessor. The valves 80 and 81, diaphragm pump 84 and fluid delivery part 85 are secured to plate structure 11 by means of bolts 112 and 113 and nuts 114 and 115 which extend through holes in metal plates 116 and 117 and holes 76 and 77 (FIGS. 1a–1e) in plate structure 11. The plate layer 78 shown in FIG. 1b includes horizontal conduits 12, 10a and 10b for the A Train and B Train conduits as well as horizontal conduit 104 which services the partition valve 28. The holes shown in FIG. 1b are aligned with the same numbered holes in the remainder of the plate layers shown in FIGS. 1a, 1c, 1d and 1e.

Figure 1B:
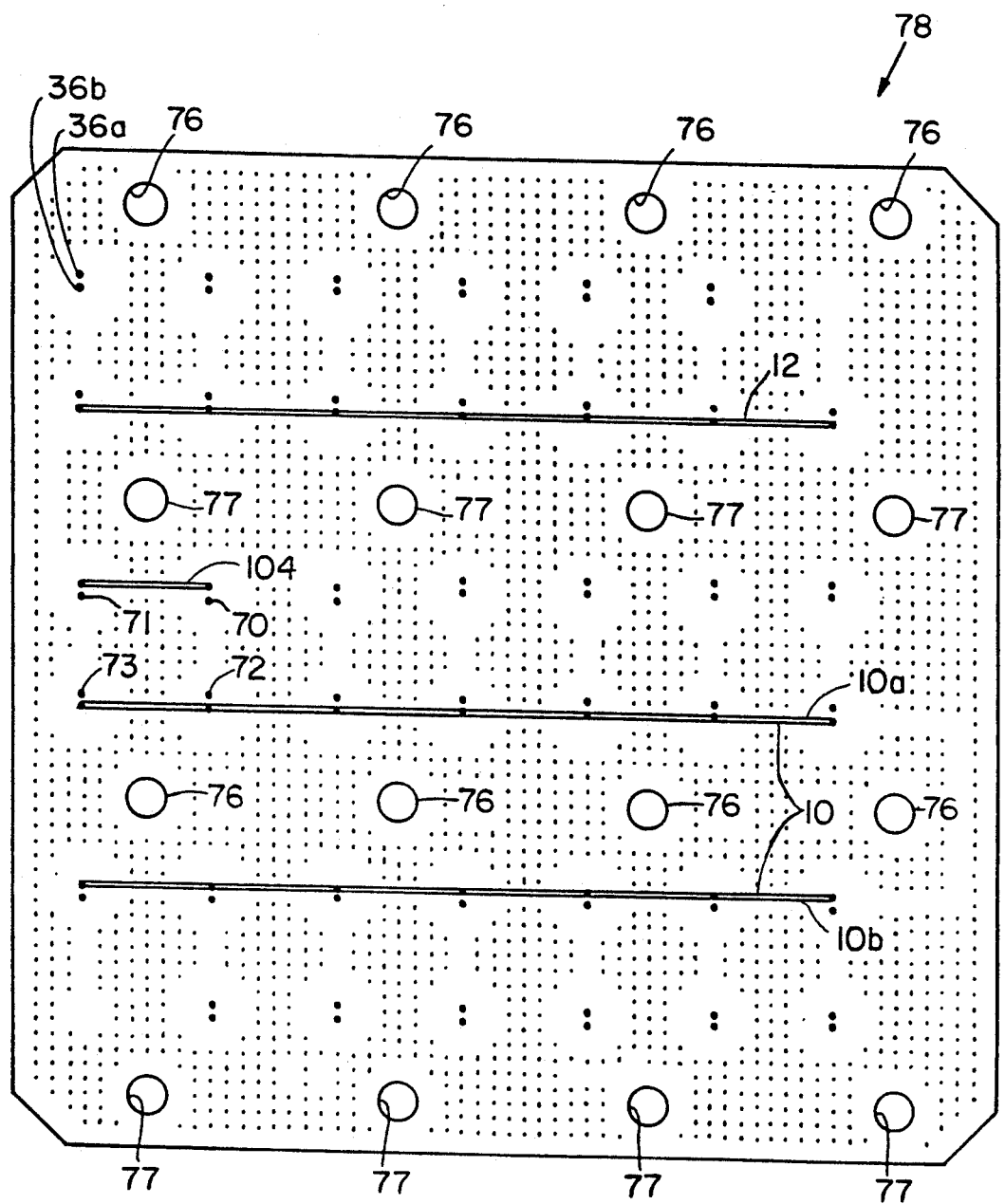
FIG. 1b is a view of a first conduit layer of the plate structure of this invention.
Figure 1C:
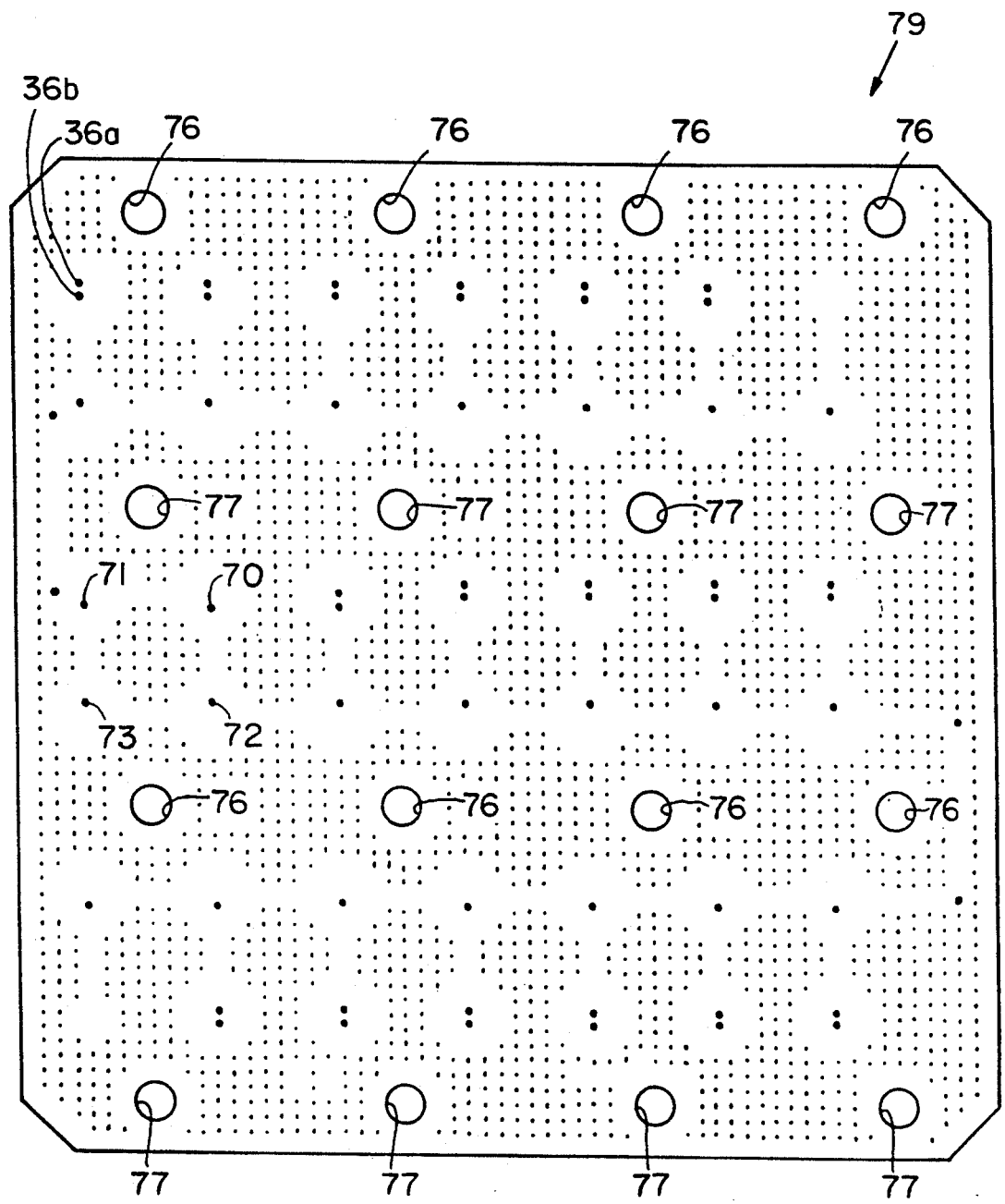
FIG. 1c is a view of the communication layer of the plate structure.
Figure 1D:
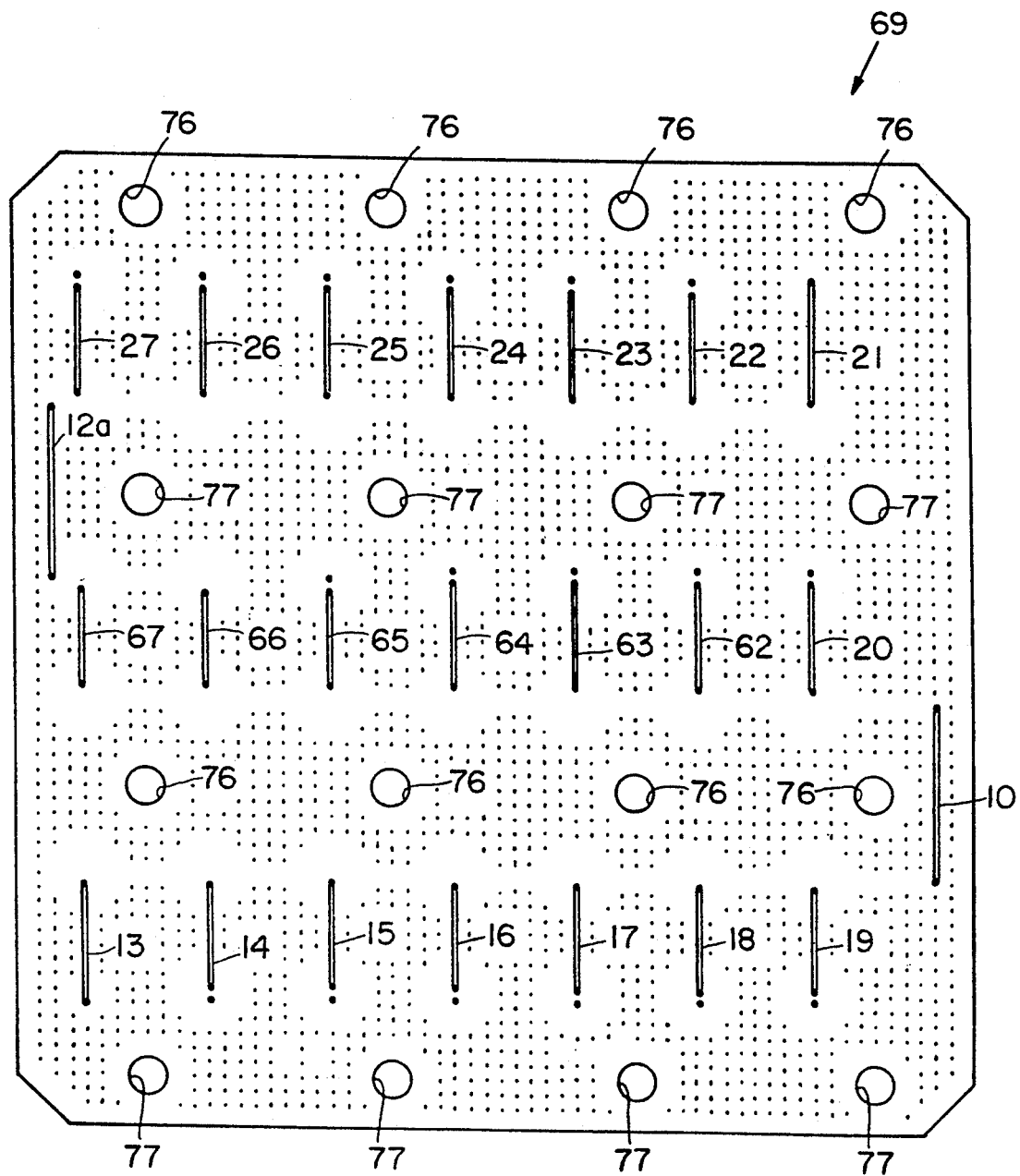
FIG. 1d is a view of a second conduit layer of the plate structure.
Figure 1E:
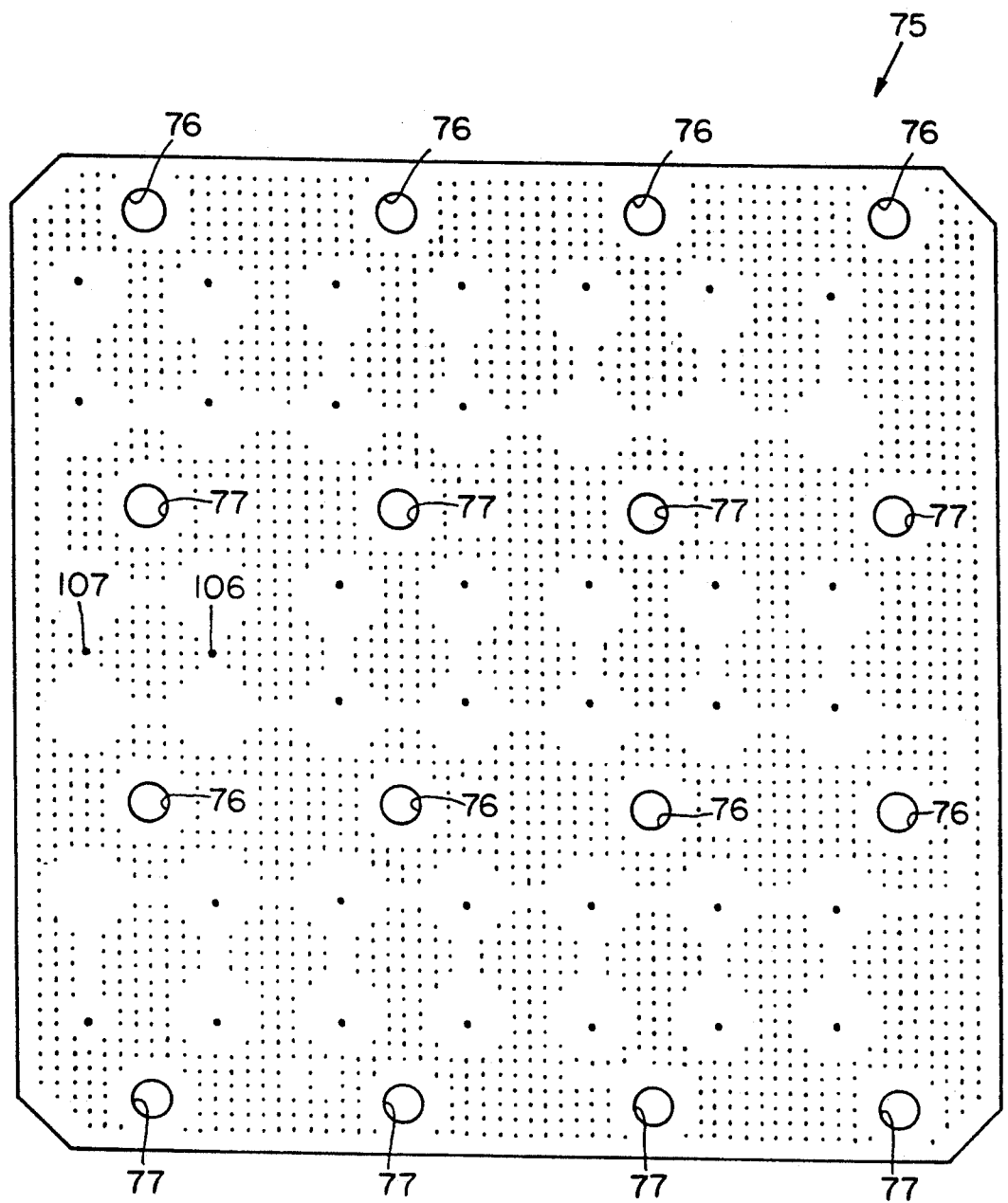
FIG. 1e is a view of the bottom layer of the plate structure of this invention.

The plate layer 79 shown in FIG. 1c separates the plate layers shown in FIGS. 1b and 1d. The numbered holes are aligned with the same numbered holes in the other plate layers. The plate layer 1c serves to provide selective fluid communication between the conduits shown in FIGS. 1b and 1d by way of the hole pairs and holes shown such as holes 36a and 36b. The plate layer 69 shown in FIG. 1d includes the vertical conduits 13 through 27, 62 through 65 and 12a for fluid reagent delivery and vertical conduits 66 and 67 which cooperate with partition valve 28. The plate layer shown in FIG. 1e includes exit ports 106 and 107 which deliver fluid from partition valve 28 on the plate structure 11 to a reaction column 29 or 30 (FIG. 1).

Figure 4:
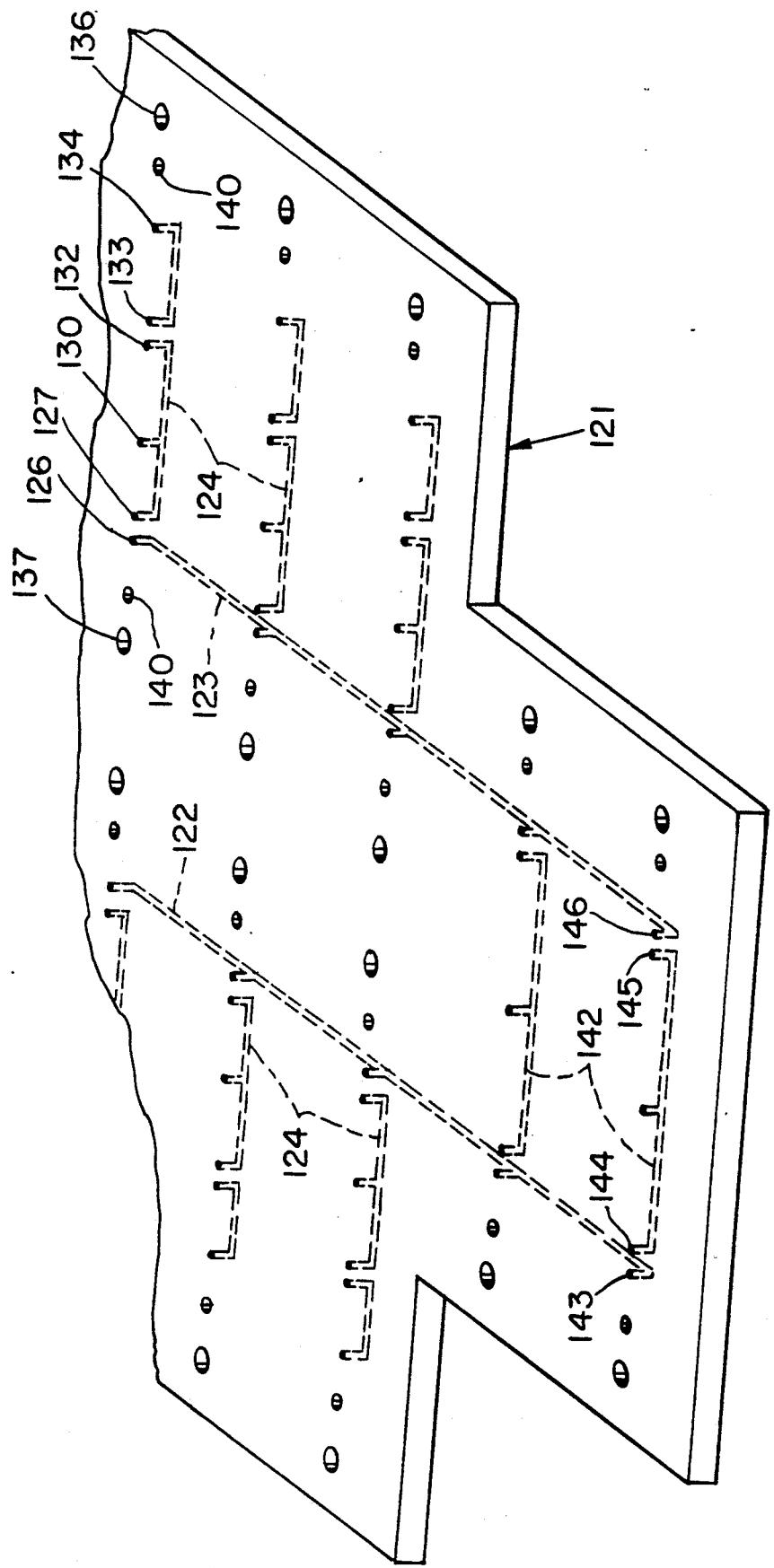
FIG. 4 is a partial view of a plate of this invention.

Referring to FIG. 4, the plate 121 includes a conduit 122 for an A train arrangement and a conduit 123 for a B train arrangement. The plate 121 includes a plurality of conduits 124 for delivering a fluid from a fluid inlet filtering 125 (FIG. 5) to either the A train 122 or the B train 123. Each conduit 124 is in fluid communication with an outlet valve 128 (FIG. 5) through holes 126 and 127, a diaphragm pump 129 (FIG. 5) through hole 130, an inlet valve 131; (FIG. 5) through holes 132 and 133 and a fluid inlet tubing 125 (FIG. 5), through hole 134.

Figure 5:
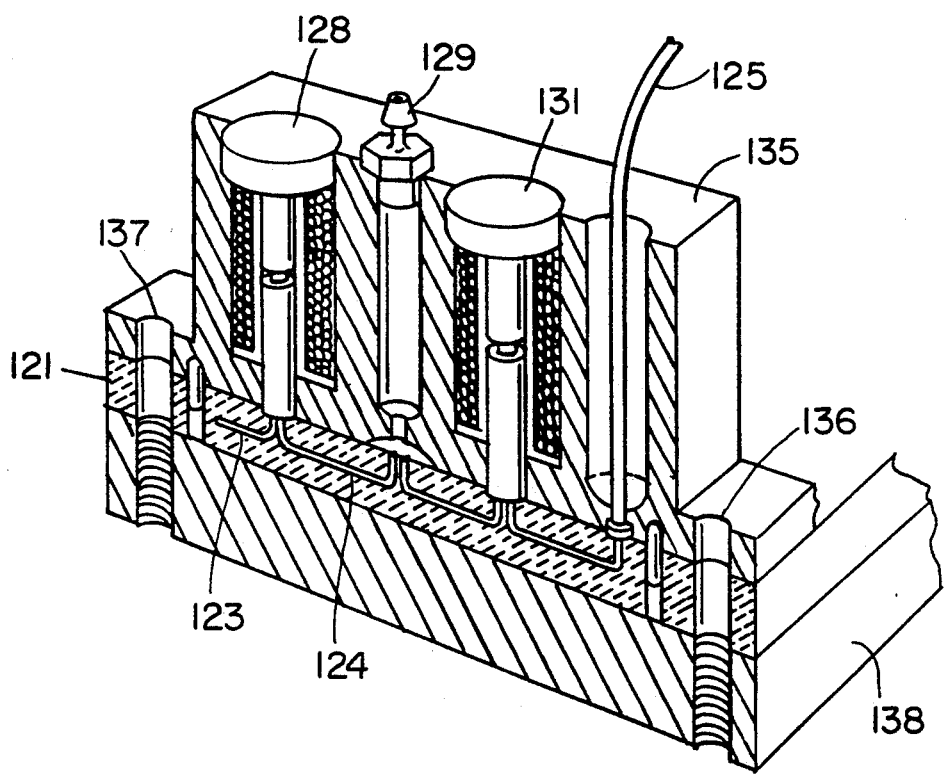
FIG. 5 is a partial view of a module useful in the present invention.

The module 135 shown in FIG. 5 is attached to plate 121 by bolts extending through holes 136 and 137 extending through module 135; plate 121 and base plate 138. The module 135 is aligned by pins extending through holes 140 extending through plate 125 and into module 135.

Figure 6:
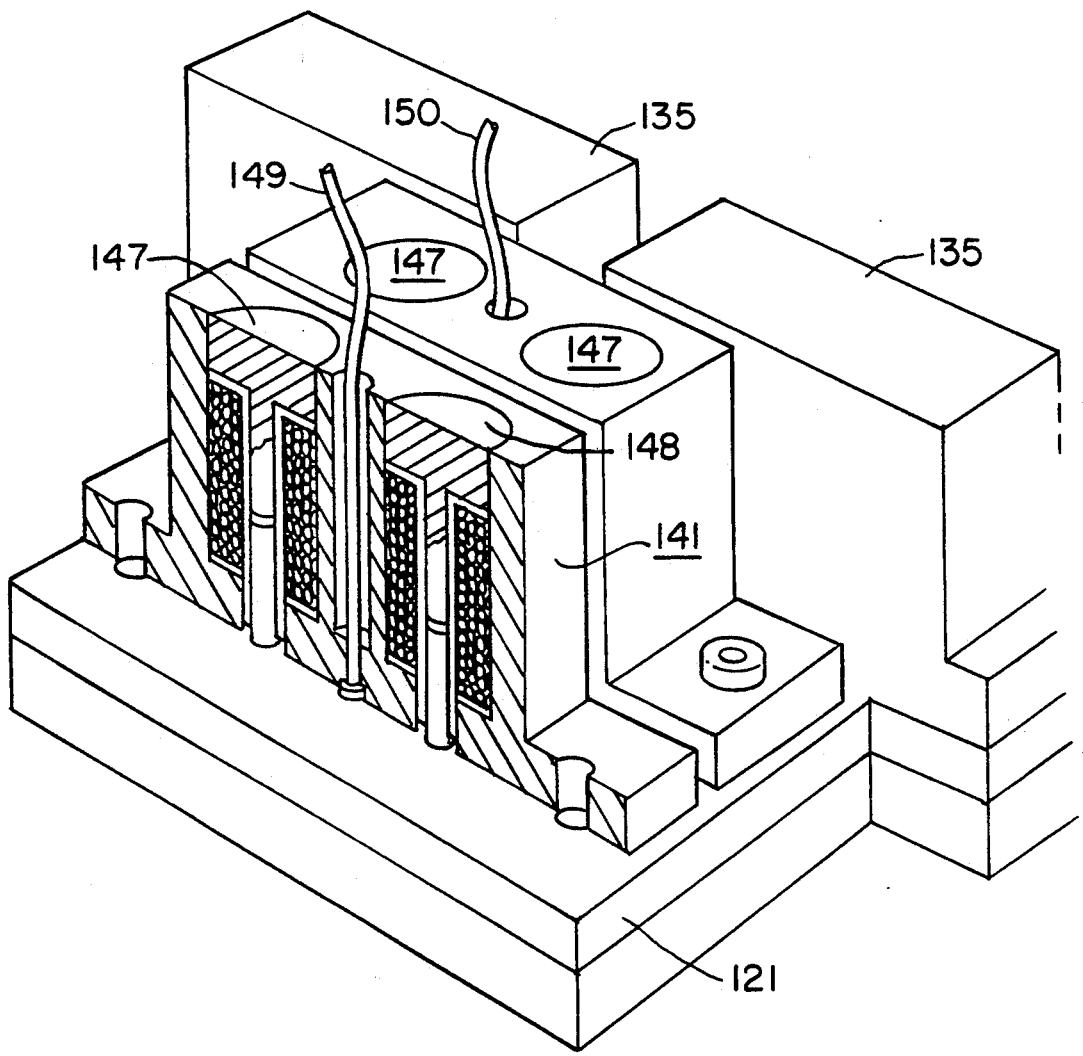
FIG. 6 is a partition valve useful in the present invention.

The partition valves 141 shown in FIG. 6 are positioned on plate 121 over conduits 142 which are in fluid communication with A train 122 through inlet valve 142 and holes 143 and 144 or B train 123 through inlet valves holes 145 and 146. The fluid is directed from either A train 122 or B train 123 to treatment reservoirs (not shown) through conduit 149 or conduit 150.

We claim:

1. The system for directing a plurality of fluids in sequence to a treatment reservoir through internal conduits in a plate means which comprises at least two fluid reservoirs and a fluid transport means for each of said fluid reservoirs comprising an electrically or pneumatically activated inlet valve, a diaphragm pump and an electrically or pneumatically activated outlet valve in fluid communication with each of said reservoirs, holes or said internal conduits plate means having internal conduits, means for maintaining elevated pressure in said fluid reservoirs, said inlet valve having a valve inlet and a valve outlet, a diaphragm positioned between said valve inlet and said valve outlet and means for positioning said diaphragm between a position for preventing fluid communication between said valve inlet and said valve outlet and for providing fluid communication between said valve inlet and said valve outlet, said diaphragm pump being positioned between and in fluid communication with said inlet valve and said outlet valve, said diaphragm pump including a plenum and a pump diaphragm and means for moving said pump diaphragm between a position for filling said plenum of fluid and for emptying said plenum of fluid, said outlet valve having a second valve inlet and a second valve outlet, a second diaphragm positioned between said second valve inlet and said second valve outlet and means for positioning said second diaphragm between a position for preventing fluid communication between said second valve inlet and said second valve outlet and for providing fluid communication between said second valve inlet and said second valve outlet, means for preventing flow of fluid from said outlet valve toward said diaphragm pump and said inlet valve, and said plate means for directing fluid from said outlet valve to a treatment reservoir through said internal conduits.

2. The system of claim 1 which includes at least one treatment reservoir and valving means for directing fluid to said at least one reservoir.

3. The system for directing a plurality of fluids in sequence to a plurality of treatment reservoirs which comprises a fluid transport means for each of said fluid reservoirs comprising an electrically or pneumatically activated inlet valve, a diaphragm pump and an electrically or pneumatically activated outlet valve in fluid communication with each of said fluid reservoirs, means for maintaining elevated pressure in said fluid reservoirs, said inlet valve having a valve inlet and a valve outlet, a diaphragm positioned between said valve inlet and said valve outlet and means for positioning said diaphragm between a position for preventing fluid communication between said valve inlet and said valve outlet and for providing fluid communication between said valve inlet and said valve outlet, said diaphragm pump being positioned between and in fluid communication with said inlet valve and said outlet valve, said diaphragm pump including a plenum and a pump diaphragm and means for moving said pump diaphragm between a position for filling said plenum with fluid and for emptying said plenum of fluid, said outlet valve having a second valve inlet and a second valve outlet, a second diaphragm positioned between said second valve inlet and said second valve outlet and electrical or pneumatic means for positioning said second diaphragm between a position for preventing fluid communication between said second valve inlet and said second valve outlet and for providing fluid communication between said second valve inlet and second valve outlet, means for preventing flow of fluid from said outlet valve toward said diaphragm pump, plate means including passageways for providing fluid communication between said inlet valve, said diaphragm pump and said outlet valve, a first common channel in said plate means for a first set of fluids, a second common channel in said plate means for a second set of fluids, means for directing fluids from said first common channel to one of a plurality of treatment reservoirs and from said second common channel to a second treatment reservoir.

4. The system of claim 1 wherein said electrical means comprises a solenoid.

5. The system of claim 2 wherein said electrical means comprises a solenoid.

6. The system of claim 3 wherein said electrical means comprises a solenoid.

7. The system of any one of claims 1, 2, 3, 4, 5 or 6 wherein said inlet valve, said diaphragm pump and said outlet valve are positioned on one surface of said plate.

8. The system of any one of claims 1, 2, 3, 4, 5, or 6 wherein said inlet valve and said outlet valve are positioned on a first surface of said plate and said diaphragm pump is positioned on a second surface of said plate.

* * * * *